(12) United States Patent
Hamilton

(10) Patent No.: US 6,383,198 B1
(45) Date of Patent: May 7, 2002

(54) FLEXIBLE VACUUM GRABBER FOR HOLDING LESIONS

(75) Inventor: Peter Hamilton, East Bridgewater, MA (US)

(73) Assignee: SciMed Life System, Inc., Maple Grove, MN (US)

( * ) Notice: Subject to any disclaimer, the term of this patent is extended or adjusted under 35 U.S.C. 154(b) by 0 days.

(21) Appl. No.: 09/456,835

(22) Filed: Dec. 7, 1999

(51) Int. Cl.[7] .............................................. A61B 19/00
(52) U.S. Cl. ........................................ 606/115; 606/110
(58) Field of Search ................................ 606/115, 110, 606/113, 114, 127

(56) References Cited

U.S. PATENT DOCUMENTS

| | | | |
|---|---|---|---|
| 3,495,593 A | * | 2/1970 | Snyder ........................ 606/115 |
| 4,146,019 A | | 3/1979 | Bass et al. |
| 4,468,216 A | | 8/1984 | Muto ............................ 604/43 |
| 4,815,450 A | | 3/1989 | Patel |
| 5,190,542 A | * | 3/1993 | Nakao et al. .................. 606/47 |
| 5,279,548 A | | 1/1994 | Essig et al. |
| 5,336,227 A | * | 8/1994 | Nakao et al. ................. 606/114 |
| 5,417,697 A | * | 5/1995 | Wilk et al. .................... 606/113 |
| 5,423,830 A | | 6/1995 | Schneebaum et al. ....... 606/115 |
| 5,441,503 A | * | 8/1995 | Considine et al. ........... 606/115 |
| 5,486,182 A | * | 1/1996 | Nakao et al. ............. 606/114 |
| 5,759,187 A | * | 6/1998 | Nakao et al. ............... 606/114 |
| 5,997,547 A | * | 12/1999 | Nakao et al. ................ 606/114 |

FOREIGN PATENT DOCUMENTS

| | | |
|---|---|---|
| WO | 95/32011 | 11/1995 |
| WO | 97/17021 | 5/1997 |
| WO | 97/26828 | 7/1997 |

* cited by examiner

Primary Examiner—Gene Mancene
Assistant Examiner—Michael B. Priddy
(74) Attorney, Agent, or Firm—Fay Kaplun & Marcin, LLP

(57) ABSTRACT

A grabbing device includes a transparent flexible cup that can be placed adjacent to a selected region of an inner surface of a body cavity. The flexible cup is visually put in place by the surgeon, and a vacuum is applied to draw a selected amount of tissue into the flexible cup, so that it may, e.g., be excised. The device may also retrieve the tissue excised from the body cavity.

16 Claims, 3 Drawing Sheets

FLEXIBLE VACUUM GRABBER FOR HOLDING LESIONS

The present invention is directed to a vacuum grabbing device used to grip and maneuver a suspect area within a body cavity. More specifically, the invention is directed to a vacuum device for gripping a suspect lesion found in a body cavity and positioning it so that it can be excised and withdrawn from the body cavity.

DESCRIPTION OF RELATED ART

Endoluminal procedures have become very common, and millions of these procedures are performed each year in hospitals around the world. An endoluminal procedure is a medical procedure that takes place within one of the many tube-like cavities, also called lumens, that are present within the human body. Endoluminal procedures may take place in vascular, gastrointestinal, or air exchange lumens, and may involve disease diagnosis as well as treatment of certain diseases.

Endoluminal procedures are often performed by using a device known as the endoscope. An endoscope is a tube, either rigid or flexible, which is introduced through an opening into a lumen in the human body. In the case of the gastrointestinal passage, the endoscope can be inserted either through the mouth or through the rectum. The endoscope may be used simply to hold the lumen open for examination, but often also carries light and vision systems, so that the operator can see within the lumen. The endoscope also often includes a working channel, usually formed within the body of the endoscope, so that the surgeon can insert and withdraw other instruments and diagnostic or treatment devices through the endoscope, to easily reach the position within the lumen being observed by the endoscope.

One important use of the endoscope is to allow the surgeon to view the patient internally, even when the portion of the patient's body cavity to be viewed is not in a direct line of sight from outside of the body. For this purpose, endoscopes typically contain a lens coupled to a visual display device by fiber optic cables, so that the body cavity in front of the endoscope can be remotely viewed on a TV screen. This common procedure is known as laparoscopy, and involves inserting the endoscope into the patient through a small incision made by the doctor, or alternatively through natural body openings like the colon or the esophagus.

Another common application of endoluminal procedures is the removal of tumors or of suspected tumor lesions inside the body cavity. In a conventional retrieval operation, an endoscope is inserted into an internal cavity of the patient, such as the colon. The endoscope is used to identify and locate the suspect region within the internal cavity, so that the suspect area can be removed. Conventionally, graspers have been used to grip tissue and draw it into a device for excision. Staples are then used to close the opening so that it may heal more effectively. The graspers are manipulated from outside the body and the cutting and stapling operations also are controlled and manipulated from outside the patient's body. Tiny grippers are generally used to grasp the lesion, but their positioning and the amount of tissue they grip is inaccurate, and often too much or too little tissue is removed.

The use of endoscopes typically reduces the size of the incision needed to perform a surgical procedure, thus allowing the patient to recover faster. In some cases no incision is necessary, since the endoscope is introduced through an existing body opening. Various types of tools such as cutters, vacuum suction devices, and other tools can be inserted through a working channel of an endoscope, and can be operated by the surgeon as they are guided to the appropriate section of the body cavity through the working channel of the endoscope. The tools are manually steered by the surgeon from the proximal end of the endoscope, i.e., the end remaining outside of the body. Other devices such as fiber optic cables used to carry illumination and images are generally part of the endoscope itself, and do not intrude in the working channel of the endoscope.

One specific tool that can be used in conjunction with the endoscope is the full thickness resectioning device, or FTRD. The FTRD is inserted in the body cavity, and has a working channel through which an endoscope and other tools can be inserted. The endoscope is advanced under visual observation until a desired location is visible. The FTRD is then pushed along the endoscope to the proper location within the body cavity, at which point other devices may be inserted through the working channel of the FTRD to the endoscope's location. The tissue to be removed is drawn into a chamber of the FTRD and then cut away from the surrounding healthy tissue while ensuring that no part of the tissue to be removed remains within the body cavity. The FTRD simultaneously staples together the severed sides of the healthy tissue to close up the wound and promote healing. Alternatively, the tissue may be stapled around the tissue to be removed before cutting. This procedure may eliminate the need for surgery and expedites recovery. However, one difficulty of using the FTRD to remove a tumor is that it may be difficult to bring the entire tumor into the chamber, and to ensure that no part of the tumor has been left in the body cavity.

When a biopsy or a resectioning is performed either using an FTRD or another biopsy device, the device is required to grip the suspect tissue before it is cut away. When the FTRD is used, the wound left by the removal of a large suspect section of tissue is closed by stapling together the surrounding healthy tissue so it may heal more easily. However, when a biopsy is conducted, the sample taken is generally much smaller, and therefore it is not necessary to use staples to close the wound. In both cases, it is important to grip the proper amount of tissue, so that the suspect portion of body cavity tissue is accurately pulled away from the wall of the body cavity lumen.

SUMMARY OF THE INVENTION

The present invention is directed to a vacuum grabber device that substantially obviates one or more of the problems due to the limitations and disadvantages of the related art, and can be used to more easily and accurately remove suspect areas in body cavities. Additional features and advantages of the invention will be set forth in the description which follows, and in part will be apparent from the description, or may be learned by practice of the invention. Other advantages of the invention will be realized and obtained by the apparatus and method particularly pointed out in the written description and claims hereof, as well as the appended drawings.

To achieve these and other advantages and in accordance with the purpose of the invention, as embodied and broadly described, the invention is a vacuum grabber device adapted for use with an insertion device inserted in the body cavity, comprising a vacuum line slidable within a working channel of the insertion device and having a distal end insertable in the insertion device, a substantially transparent flexible cup attached to the distal end of the vacuum line foldable to fit within the working channel and deployable to a configuration substantially funnel shaped, means for applying a vacuum to the flexible cup, and means for positioning the deployed flexible cup within the body cavity such that the flexible cup can hold a selected inner portion of the body cavity by vacuum, and can be at least partially withdrawn into the insertion device while holding the selected inner portion. A vision device is used to view the selected inner portion of the body cavity through the flexible cup.

In another embodiment, the invention is a method for removing a selected portion of tissue from a surface of a body cavity, having the steps of inserting into the body cavity an insertion device, advancing through the insertion device a substantially transparent flexible cup in a folded configuration within the insertion device, deploying from the insertion device the flexible cup in a substantially funnel shaped configuration, and visually positioning the deployed flexible cup adjacent to the selected portion of tissue by observing the selected portion of tissue through the flexible cup. The steps of the method also include applying a vacuum pressure through the flexible cup to draw the selected portion of tissue into the flexible cup, and at least partially withdrawing the flexible cup proximally into the insertion device to draw the selected portion of tissue into a desired position relative to the insertion device.

It is to be understood that both the foregoing general description and the following detailed description are exemplary and explanatory and are intended to provide further explanation of the invention as claimed.

BRIEF DESCRIPTION OF THE DRAWINGS

The accompanying drawings are included to provide a further understanding of the invention and are incorporated in an constituent part of this specification, illustrate several embodiments of the invention and together with a description serve to explain the present invention. In the drawings.

DETAILED DESCRIPTION OF THE INVENTION

The present invention provides a device and method to ensure that a selected inner portion of a body cavity is gripped, so that a suspect area possibly containing a tumor as well as a small surrounding area of healthy tissue may be removed. The additional amount of healthy tissue being removed is necessary to provide a safety margin portion of tissue, to ensure that all of the suspect area has been cut away from the body cavity. The invention also ensures that the entire tissue sample that has been cut is actually removed from the body cavity before the endoscope and associated tools are removed. The invention prevents the cut tissue from falling out of the device and being left within the body cavity, so that further study of the removed tissue to perform a diagnosis is possible. The invention protects the cut tissue from the surrounding area while withdrawing it from the body cavity, so that the sample is not contaminated by extraneous materials on the way out of the body cavity. In addition, the invention limits the amount of healthy tissue surrounding the suspect area that is damaged when the suspect area is removed from the body cavity.

Figure 1:
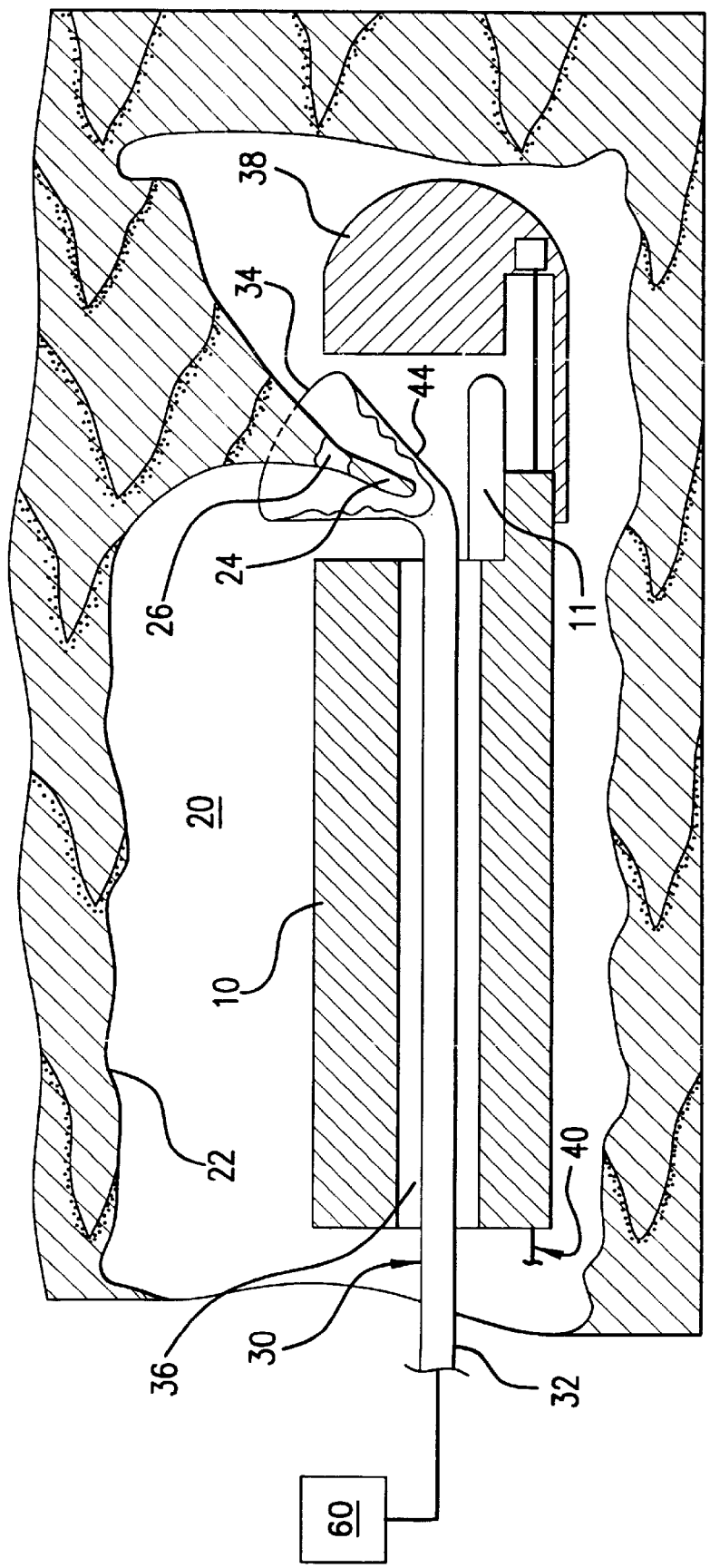
FIG. 1 is a diagram showing a cut-away view of the vacuum grabber device according to one embodiment of the invention, deployed from an insertion device located within a body cavity.

FIG. 1 shows a diagram of an embodiment according to the invention, used in conjunction with a FTRD to remove a suspect area from a body cavity. FTRD 10 is inserted within a body cavity 20 either through an incision made by the surgeon or through a natural opening of the cavity. Body cavity 20 is roughly tubular in shape, and has an inner surface 22 that includes a suspect area 24. The suspect area 24 may be either a lesion that has to be removed and analyzed to determine if it is cancerous, or a growth such as a polyp that has to be removed, or from which a biopsy must be taken. The vacuum grabber device 30 is inserted inside a working channel 36 formed in the center of the FTRD 10, and includes a vacuum line 32 and a flexible cup 34 attached to the vacuum line 32.

Figure 2:
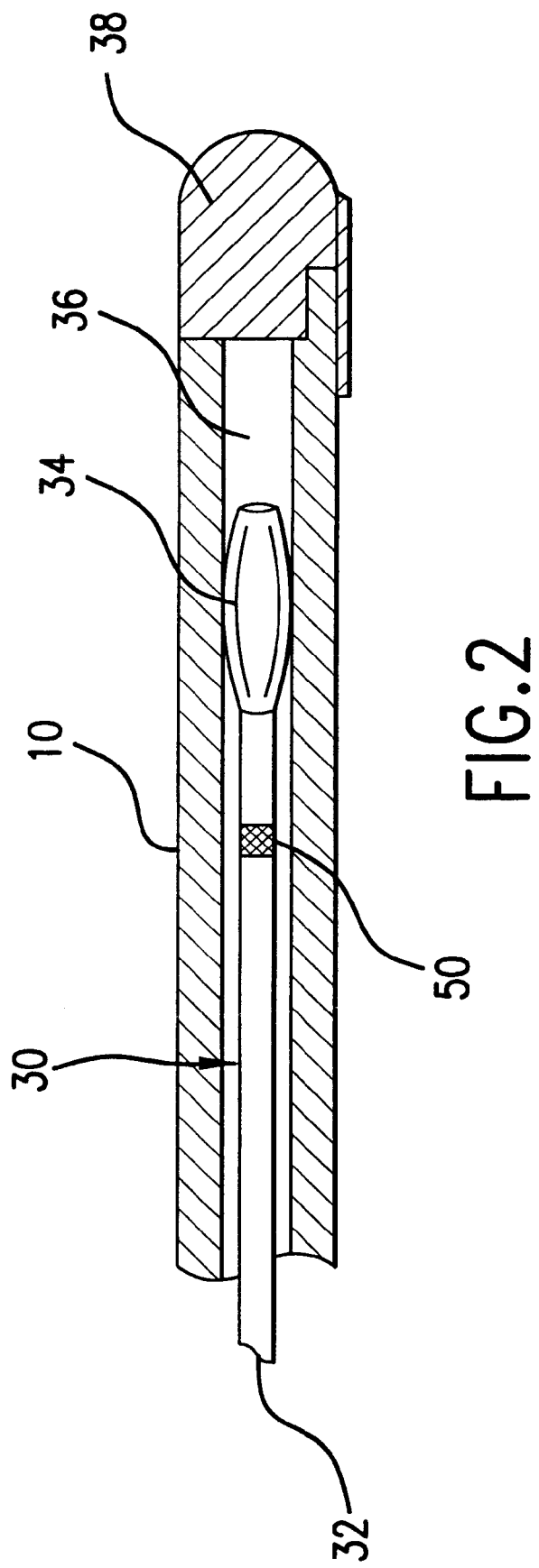
FIG. 2 is a diagram showing a cut-away view of the vacuum grabber device according to an embodiment of the present invention, in a folded configuration within the insertion device.

The vacuum grabber device 30 is adapted to be inserted in the FTRD 10, so that both components can be introduced within the patient's body cavity 20. The distal end of FTRD 10 is placed in position near the suspected lesion 24 located on inner wall 22 of the body cavity 20, and the vacuum grabber device 30 can thus also reach the suspected lesion 24. When vacuum grabber device 30 is inserted in the working channel of FTRD 10, the flexible cup portion 34 is in the folded configuration, so that it can more easily travel through working channel 36. FIG. 2 shows this configuration. Once FTRD 10 is positioned within the body cavity 20 near the suspect region 24, head assembly 38 of the FTRD 10 is opened, for example by pushing on control wire 40 which connects the head assembly 38 to an area outside of the patient's body. Once head assembly 38 is opened, vacuum grabber device 30 is pushed outside of FTRD 10 through an opening between the main body of FTRD 10 and the head assembly 38.

Although the present embodiment of the invention is described in conjunction with a FTRD, other insertion devices capable of excising a portion of tissue within a body cavity can also be used. The present invention is thus generally usable to capture a suspect portion of the inner surface of a body cavity so that treatment, observations or removal to the suspect portion of tissue may be performed.

In another embodiment according to the invention, vacuum grabber device 30 could be inserted into the patient's body cavity 20 by means of an insertion device other than an FTRD that can shield the vacuum line 32 and the flexible cup 34. Once the insertion device reaches the suspect area of interest, an opening could be made in the insertion device to eject the vacuum grabber device 30. For example, the insertion device could be similar to the FTRD, but without the ability to cut and staple the tissue of the body cavity 20. As described above, the cutting and stapling functions could be performed by additional tools inside or adjacent to the insertion device.

Figure 3:
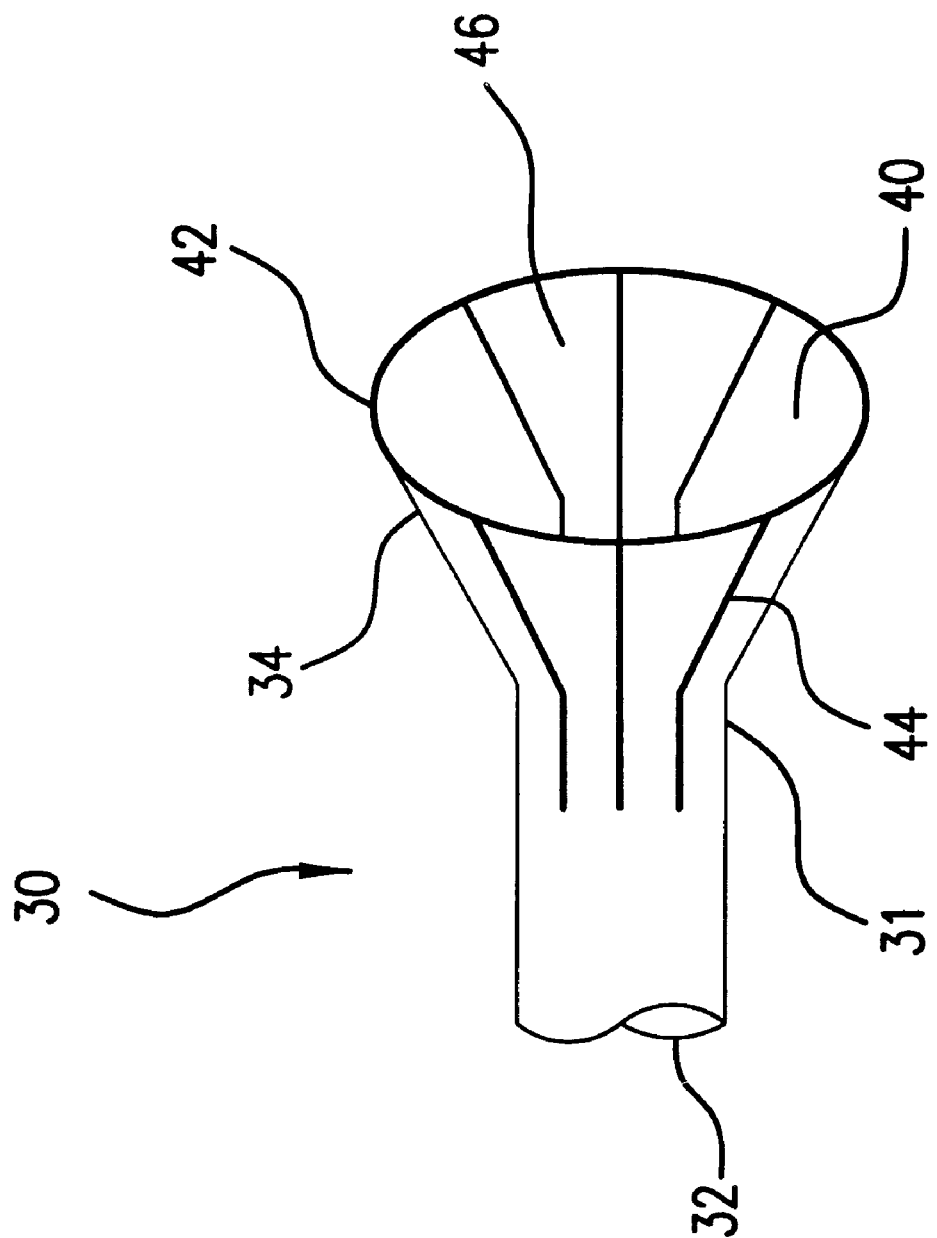
FIG. 3 is a diagram showing the flexible cup of the vacuum grabber device shown in FIG. 2, in a deployed configuration.

As shown in FIGS. 1 and 3, vacuum grabber device 30 is pushed outside of the opening made between head assembly 38 and the main body of FTRD 10, at which point the folded flexible cup 34 automatically deploys into a substantially funnel shaped configuration.

In a preferred embodiment according to the invention shown in FIG. 3, the flexible cup in the deployed configuration has a substantially funnel shape, with a small opening 31 connected to the vacuum line 32, and a larger opening 46 adapted to be placed over the suspect region 24 that requires treatment. The flexible cup can have openings that are not round, as long as it can be connected to the source of vacuum, and the large opening can cover the desired portion of tissue.

After exiting the working channel 36 of FTRD 10, the flexible cup 34 opens to its deployed configuration automatically, due to the force exerted by resilient elements that make up the structure of flexible cup 34. For example, a resilient ring-like structure 42 can be disposed near the large opening 46, so that once it is no longer constrained, flexible cup 34 will open to its funnel configuration. In addition, or instead of resilient ring 42, several resilient ribs 44 can be located on the sides of flexible cup 34 to force it in the deployed configuration once its no longer constrained within working channel 36. The resilient elements can be embedded in a transparent membrane 40 forming the flexible cup, or can be placed inside or outside of membrane 40. Other configurations of resilient elements 42 and 44 could be used, such as spiral configurations, multiple rings, or any other known configurations that will open flexible cup 34 to its proper shape.

The vacuum grabber device 30 can be moved axially along the inside of body cavity 20 by simply pushing or pulling on the vacuum line 32. In addition, in one embodiment according to the invention, flexible cup 34 is placed at an angle from the center line of vacuum line 32, so that rotating vacuum line 32 will cause large opening 46 of flexible cup 34 to sweep in a generally circumferential direction along the inner surface 22 of body cavity 20. This configuration allows large opening 46 to be placed over a selected portion of the body cavity.

In one preferred embodiment according to the invention, the flexible cup 34 is made of a flexible polymer that is clear, for example, a plasticized silicon material. Other materials could be used that are transparent and substantially air tight, so that a vacuum can be applied and held by the flexible cup. The materials preferably can insulate the suspect lesion or other tissue that was removed from the surrounding body cavity, so that it will not be contaminated by extraneous materials when it is withdrawn from the body. The flexible cup must be sufficiently transparent so that the tissue in question can be seen through the flexible cup. For example, an endoscope could be used to look at the tissue through membrane 40.

In yet another embodiment according to the invention, a mesh 50 or other type of screen can be located in the vacuum line 32, or near the small opening of flexible cup 34. This screen is designed to prevent portions of the tissue that was removed from traveling down the vacuum line, and can also be used to form a holding area for the tissue, so that it will be protected from contamination by vacuum line 32 and by the membrane 40 of flexible cup 34.

The operation of vacuum grabber device 30 will now be explained with reference to FIGS. 1 through 3. FTRD 10 or another type of insertion device is inserted in body cavity 20 and is navigated by the surgeon to a location near suspect lesion 24, located on inner surface 22 of the body cavity 20. At this point, vacuum grabber device 30 is inside working channel 36 of FTRD 10, and flexible cup 34 is in the folded configuration shown in FIG. 2. When FTRD 10 is in place, head assembly 38 is opened, and flexible cup portion 34 is ejected outside of FTRD 10.

As explained above, flexible cup 34 opens in its funnel configuration once no longer constrained in working channel 36. The surgeon can look for suspect lesion 24 through the endoscope 11 which is also inserted through the working channel of FTRD 10, and can position flexible cup 34 over the suspect lesion by rotating, pulling and pushing vacuum line 32. By looking with endoscope 11 through transparent membrane 40 of flexible cup 34, the surgeon can position the funnel-like flexible cup over the suspect lesion 24, and can start applying a vacuum by operating vacuum means, such as vacuum pump 42, which can provide both an adjustable vacuum and positive pressure in vacuum line 32.

While looking through transparent membrane 40 of flexible cup 34, the surgeon can vary the amount of vacuum and positive pressure applied to the flexible cup 34, so that the selected inner portion of the body cavity containing the suspect lesion 24 as well as a safety margin portion 26 of healthy tissue surrounding the suspect lesion 24 is gripped and contained within flexible cup 34. In a preferred embodiment, the safety margin portion 26 can extend beyond lesion 24 by about 3 mm to 6 mm.

By looking with endoscope 11 through transparent membrane 40 of flexible cup 34, the surgeon can position the funnel-like flexible cup over the suspect lesion 24, and can start applying a vacuum by operating vacuum means, such as vacuum pump 60, which can provide both an adjustable vacuum and positive pressure in vacuum line 32.

The surgeon at that point can operate cutting device 56 that is part of the FTRD 10, to separate the selected inner portion of the body cavity from the rest of inner surface 22. For example, cutting device 56 can be an extendable and movable blade. A stapling portion 58 of FTRD 10 can be used at that point to close the wound left by the removed portion of the body cavity, so that healing will be promoted. The specific configuration of cutting device 56 and stapling portion 58 can vary, as long as a portion of the body cavity drawn inside FTRD 10 is cut and the severed sides of the remaining healthy tissue are stapled together.

The selected inner portion of body cavity containing suspect lesion 24 as well as a margin of safety portion 26 of healthy tissue is thus held by vacuum within flexible cup 34, and after cutting is withdrawn from the body of the patient while being protected from contamination by membrane 40 of flexible cup 34. A pathology study of suspect lesion 24 can then be carried out without the concern that the results may be affected by possible contamination of the sample.

According to one embodiment of the invention, the selected inner portion of body cavity that was removed can be held near the flexible cup 34 by a screen 50 acting as a sample catcher. Alternatively, the selected inner portion can be drawn by vacuum all the way down vacuum line 32, and can be collected outside of the body at the proximal opening of vacuum line 32.

In one embodiment, FTRD 10 can be inserted into the patient and can carry an endoscope in a working channel of the FTRD. Alternatively, the FTRD could be inserted separately from the endoscope, in the same cavity. The important consideration in positioning the endoscope is that the surgeon must be able to see the flexible cup 34 and the suspect lesion area 24, so that the transparent flexible cup 34 can be correctly placed over the lesion area 24, and the selected inner portion of the body cavity can be drawn within flexible cup 34.

In yet another embodiment according to the invention, flexible cup 34 can be provided in various sizes, so that the appropriate cup can be applied to different size lesions to ensure that the entire lesion plus a safety margin of healthy tissue can be drawn inside the flexible cup 34. In addition, for cases where the lesion 24 has a very irregular shape, specially designed flexible cups could be used, either having very high flexibility or having specific shapes of the large opening 46 to accommodate the irregularly shaped lesion. In the latter case, flexible cup 34 should have dimensions commensurate with the largest dimension of the lesion, such as the lesion length or diameter. An increased vacuum may also be necessary to firmly hold a lesion having an irregular shape within flexible cup 34.

It will be apparent to those skilled in the art that various modifications and variations can be made in the structure and methodology of the present invention, without departing from the spirit or scope of the invention. Thus, it is intended that the present invention covers the modifications and variations of this invention provided they come within the scope of the appended claims and their equivalents.

What is claimed is:

1. A vacuum grabber device for insertion into a body cavity via an insertion device, the insertion device having a working channel extending therethrough from a proximate end to a distal end thereof, the vacuum grabber device comprising:
    a vacuum line slidable within the working channel, the vacuum line having a distal end insertable in the insertion device;
    a substantially transparent and airtight flexible cup attached to the distal end of the vacuum line, the flexible cup being foldable to fit within the working channel and, wherein when deployed from the working channel, the flexible cup is expandable into a funnel having a maximum diameter greater than that of the working channel; and
    means for applying a vacuum to the vacuum line.

2. The vacuum grabber device according to claim 1, wherein the flexible cup is formed of a clear flexible polymer.

3. The vacuum grabber device according to claim 2, wherein the clear flexible polymer is a plasticized silicon.

4. The vacuum grabber device according to claim 1, wherein the maximum diameter of the flexible cup is predetermined based on a size of the selected portion of tissue, plus a safety margin portion of tissue.

5. The vacuum grabber device according to claim 1, further comprising a sample catcher disposed between the flexible cup and the means for applying a vacuum.

6. The vacuum grabber device according to claim 5, wherein the sample catcher is a mesh disposed in the vacuum line.

7. The vacuum grabber device according to claim 1, wherein the flexible cup is biased so that, when not constrained within the working channel, the flexible cup expands to a substantially funnel shaped configuration.

8. The vacuum grabber device according to claim 7, wherein the flexible cup further comprises resilient elastic elements to bias the cup to the substantially funnel shaped configuration.

9. The vacuum grabber device according to claim 1, wherein the means for applying a vacuum is adapted to provide an adjustable vacuum pressure.

10. The vacuum grabber device according to claim 9, wherein the means for applying a vacuum may selectively provide one of a positive pressure and a vacuum.

11. The vacuum grabber device according to claim 1, wherein the flexible cup comprises a membrane adapted to prevent contamination of the selected portion of tissue drawn in the flexible cup.

12. The vacuum grabber device according to claim 1, wherein, when the flexible cup is not constrained within the working channel, the body cavity is observable by a vision device through the substantially transparent flexible cup.

13. The vacuum grabber device according to claim 1, wherein the vacuum line is adapted to be rotated about the axis of the vacuum line within the working channel.

14. The vacuum grabber device according to claim 1, wherein the flexible cup is angled about the axis of the vacuum line.

15. A vacuum grabber device for insertion into a body cavity via an insertion device, the insertion device having a working channel extending therethrough from a proximate end to a distal end thereof, the vacuum grabber device comprising:
    a vacuum line slidable within the working channel, the vacuum line having a distal end insertable in the insertion device;
    a substantially transparent flexible cup attached to the distal end of the vacuum line, the flexible cup being foldable to fit within the working channel and, wherein when deployed from the working channel, the flexible cup is expandable into a funnel; and
    means for visually positioning the deployed flexible cup adjacent to a selected portion of tissue within the body cavity, such that the body cavity is observable by a vision device through the substantially transparent flexible cup.

16. A vacuum grabber device for insertion into a body cavity via an insertion device, the insertion device having a working channel extending therethrough from a proximate end to a distal end thereof, the vacuum grabber device comprising:
    a vacuum line slidable within the working channel, the vacuum line having a distal end insertable in the insertion device;
    a flexible cup attached to the distal end of the vacuum line, the flexible cup being foldable to fit within the working channel and, wherein when deployed from the working channel, the flexible cup is expandable into a funnel having a maximum diameter greater than that of the working channel;
    means for applying a vacuum to the vacuum line; and
    a sample catcher disposed between the flexible cup and the means for applying a vacuum.

\* \* \* \* \*